United States Patent [19]

Cunnington et al.

[11] Patent Number: 5,807,803
[45] Date of Patent: Sep. 15, 1998

[54] CATALYST AND PROCESS FOR THE EPOXIDATION OF OLEFINIC COMPOUNDS

[75] Inventors: Malcolm John Cunnington, East Yorkshire; Matthew More Miller, Edinburgh; David Colin Sherrington, Glasgow; Sydney Simpson, East Yorkshire; Gunnar Olason, Glasgow, all of United Kingdom

[73] Assignee: BP Chemical Limited, England

[21] Appl. No.: 398,089

[22] Filed: Mar. 3, 1995

Related U.S. Application Data

[62] Division of Ser. No. 236,590, May 2, 1994, Pat. No. 5,420,313.

[30]    Foreign Application Priority Data

May 7, 1993  [GB]   United Kingdom ............. 9309458

[51] Int. Cl.$^6$ ....................................................... B01J 31/00
[52] U.S. Cl. ....................... 502/155; 502/150; 502/152; 502/153; 502/159; 502/162; 502/167
[58] Field of Search ................................... 502/150, 152, 502/153, 155, 159, 162, 167

[56]    References Cited

U.S. PATENT DOCUMENTS

| | | | |
|---|---|---|---|
| 3,980,662 | 9/1976 | Watanabe et al. ................... | 502/159 |
| 3,985,679 | 10/1976 | Taylor et al. . | |
| 4,066,705 | 1/1978 | Hughes . | |
| 4,077,906 | 3/1978 | Hughes . | |
| 4,098,727 | 7/1978 | Haag et al. ............................ | 502/159 |
| 4,189,448 | 2/1980 | Carlock . | |
| 4,529,824 | 7/1985 | Mimour et al. . | |
| 4,800,188 | 1/1989 | Shepherd . | |
| 4,845,252 | 7/1989 | Schmidt et al. . | |
| 5,141,911 | 8/1992 | Meunier et al. ...................... | 502/159 |
| 5,166,372 | 11/1992 | Crocco et al. . | |

FOREIGN PATENT DOCUMENTS

| | | |
|---|---|---|
| 0222167 | 5/1987 | European Pat. Off. . |
| 0283753 | 9/1988 | European Pat. Off. . |
| 032615 | 11/1989 | European Pat. Off. . |
| 51-141866 | 12/1976 | Japan . |
| 03235234 | 10/1991 | Japan . |
| 9101806 | 2/1991 | WIPO . |

OTHER PUBLICATIONS

Applied Catalysis, 26 (1986) 285–293, E. Tempesti, L. Giuffre, F. DI Renzo, C. Mazzocchia and Airoldi—Bimetallic Boron (III)—Molybdenum(VI) Catalysts as New Model Compounds in the Epoxidation of Cyclohexene.

Pure & Appl. Chem., vol. 60, No. 3, pp. 401–414, 1988—David c. Sherrington, Polymer–Supported Metal Complex Oxidation Catalysts Oxidation Communications 6, Nos. 1–4, 55–63 (1984) St. V. Kotov.

R.S. Boeva and N.D. Yordanov—Kinetic Study on the Epoxidation of Cyclohexene with t-Butylhydroperoxide in the Presence of Molybdenum–Containing Cation Exchanger as Catalyst.

Reaction Kinetics and Catalysis Letters, vol. 5, No. 3, 297–301 (1976), S. Ivanov, R. Boeva and S. Tanielyan—Catalytic Epoxidation of Propylene with tert–Butyl Peroxide in Presence of Molybednum Complexes on Polymer Carriers.

Journal of Catalysis 56, 150–159 (1970), S. Ivanov, R. Boeva and S. Tanielyan—Catalytic Epoxidation of Propylene with tert–Butyl Hydroperoxide in the Presence of Modified Carboxy Cation–Exchange Resin "Amberlite" IRC–50.

Journal of Molecular Catalysis, 11 (1981) 371–381, T. Szymanska–Buzar and J.J. Ziolkowski—Oxotrimetal Hexacarboxylates as Heterogenized Catalysts in Hydroperoxide Decomposition and Olefin Epoxidation Reactions.

Neogi, Macromolecular Organometallic Catalysis II. Epoxidation Using a Polymeric Quaternary Ammonium Hydrogen Tungstate Catalyst.

Recl. Trav. Chim. Pays–Bas, 109(11), 537–51 (1990) On the Mechanism of Epoxidation of Alkenes with Hypochlorite, Catalysed by Manganese(III) tetraarylporphyrins. no month avaliable.

Journal of Catalysis 131, 115–126 (1991), D.C.—Sherrington and S. Simpson—Polymer–Supported Mo and V Cyclohexene Epoxidation Catalysts: Activation, Activity and Stability no month available.

D. Lindsay, Ph.D. Thesis, University of Strathclyde (1986) Summary no month available.

D. Lindsay, D. Sherrington, J. Greig and R. Hancock, J. Chem. Soc., Chem. Commun., 1270–1272 (1987) no month available.

T. Yokohama, M. Nishizawa, T. Kimura and T.M. Suzuki, Chem. Lett., 1703–1706 (1983) no month available.

T. Yokohama, M. Nishizawa, T. Kimura and T.M. Suzuki, Bull. Chem. Soc. Jap., 58, 3271–3276 (1985) no month available.

K. Zhang, G.S. Kumar and D.C. Neckers, J. Polym. Sci: Pol. Chem, 23, 1213–1220 (1985) no month available.

M. Goto and S. Goto, React. Kinet. Catal Lett., 39(2). 267–271 (1989) no month available.

Y. Kurusu, Y. Masuyama, M. Saito and S. Saito, J. Molec. Catal 37, 235–241 (1986) no month available.

R.T. Stamenova. C.B. Tsvetanov, K.G. Vassilev, S.K. Tanielyan S.K. Ivanov, J. Appl. Polym. Sci., 42, 807–812 (1991) no month available.

M. Chanda, and G.L. Rempel, J. Polym. Sci., Part A: Polym. Chem. 27, 3237–3250 (1989) no month available.

G.G. Allan and A.N. Neogi, J. Phys. Chem., vol. 73, No. 6, 2093–2095 (1969) no month available.

(List continued on next page.)

Primary Examiner—Elizabeth D. Wood
Attorney, Agent, or Firm—Brooks Haidt Haffner and Delahunty

[57]    ABSTRACT

A catalyst composition having high epoxidation activity and resistant to leaching of its metal comprises molybdenum, vanadium, tungsten and/or titanium complexed to an organic or inorganic support through the intermediacy of an imidazole ligand. The catalyst may be used in epoxidation of olefinic compounds.

5 Claims, No Drawings

OTHER PUBLICATIONS

S.K. Tanelyan, R.S. Boeva and S.K. Ivanov, Dokl. Bolg. Ahad. Nauk 31, 67–69 (1978) no month available.

S. Tanelyan, S. Ivanov and R. Boeva, Neftekhimya, 18, 760 (1978) no month available.

G.L. Linden and M.F. Farona, J. Catal., 48, 284(1977) no month available.

J. Sobczak and J.J. Ziolkowski, J. Molec. Catal., 3, 165–172 (1977/78) no month available.

R. Boeva, S. Kotov and N.I. Jordanov, React. Kinet. Catal. Lett., 24, 239–242 (1984) no month available.

S. Bhaduri, A. Ghosh and H. Khwaja, J. Chem. Soc. Dalton, 447;451 (1981) no month available.

S. Bhaduri and H. Khwaja, J. Chem. Soc. Dalton Trans., 415–418 (1981) no month available.

D.C. Sherrington and P Hodge, "Polymer Supported Reactions in Organic Synthesis" J. Wiley Chichester (1980) no month available.

P.E. Cassidy, "Thermally Stable Polymers", Marcel Dekker, New York (1980) no month available.

P. Hoffman and B. Meunier "Preparation and Catalytic Activities of Molybdenum Halogenated Porphyrins in Hydrogen Peroxide Olefin Oxidations"New Journal of Chemistry, 16, pp. 559–561 (1992) no month available.

T Brock, D. C. Sherrington and H.G. Tang, Polymer, 32, 353–357 (1991) no month available.

H.G. Tang, Ph.D. Thesis, University of Strathclyde (1991) (Abstract Only) no month available.

N.H. Li and J.M.J. Frechet, J. Chem. Soc. Chem. Comm., 1100 (1985) no month available.

J.M.J. Frechet, A. Deratani, G. Darling, P. Lecavalier and N.H. Li, Mackromol. Chem. Mekromol. Symp., 1, 91–100 (1986) no month available.

T. Brock, Ph.D. Thesis, University of Stratclyde (1991) (abstract only) no month available.

CATALYST AND PROCESS FOR THE EPOXIDATION OF OLEFINIC COMPOUNDS

This application is a division of application Ser. No. 08/236,590, filed May 2, 1994 and now U.S. Pat. No. 5,420,313.

This invention relates to a catalyst and process for the epoxidation of olefinic compounds.

Epoxidation of olefinic compounds is a well known process which is operated industrially. For example the epoxidation of propylene to propylene oxide using alkyl hydroperoxide is known to be catalysed by a soluble molybdenum catalyst and by a heterogeneous titanium/silica catalyst.

Sherrington and Simpson describe in Journal of Catalysis 131 115–126 (1991) polymer-supported molybdenum and vanadium cyclohexene epoxidation catalysts in which the metals are bound through a hydroxypropylated aminomethylpyridine ligand.

However, there remains a need for an improved heterogeneous epoxidation catalyst.

Thus, according to the present invention there is provided a catalyst composition comprising molybdenum, vanadium, tungsten and/or titanium complexed to an organic or inorganic support through the intermediacy of an imidazole ligand.

Also, according to the present invention there is provided a process for the epoxidation of olefinic compounds which process comprises reacting the olefinic compound with a peroxide in the presence of a catalyst composition comprising molybdenum, vanadium, tungsten and/or titanium complexed to an organic or inorganic support through the intermediacy of an imidazole ligand.

The present invention provides a novel catalyst which has high epoxidation activity and is resistant to leaching of its metal in use.

The catalyst composition according to the present invention preferably comprises molybdenum, vanadium and/or tungsten, most preferably molybdenum. More than one metal may be present in the catalyst composition.

The imidazole ligand may comprise unsubstituted imidazole or a substituted imidazole such as 2-pyridyl-2-imidazole, benzimidazole, 5-benzimidazole carboxylic acid and hydroxy substituted imidazoles and benzimidazoles. The imidazole ligand may be attached to the support through any part of the imidazole or substituted imidazole ligand provided that the imidazole ring is available for complexing to the metal of the catalyst. The imidazole ligand may comprise part of the support rather than being pendant thereto; for example, the imidazole may comprise part of a polymer repeating unit. A preferred class of polymers for use in the catalyst of the present invention which have an imidazole ligand as part of their polymer support repeating unit are polybenzimidazoles and in particular poly[2,2'(m-phenylene)-5,5'-benzimidazole] which is a polymer having a repeating unit represented by the formula (I):

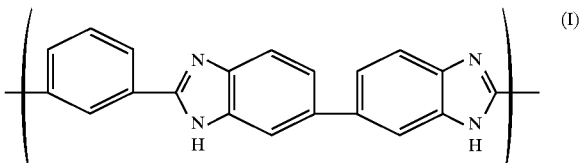

Suitably, the ligand loading in the catalyst composition is in the range 0.1 to 5 mmol g$^{-1}$ preferably 0.25 to 2.5 mmol g$^{-1}$ and the metal loading in the catalyst composition is suitably in the range 0.1 to 10 mmol g$^{-1}$ preferably, 0.1 to 5 mmol g$^{-1}$. Preferably, the ligand:metal molar ratio is in the range 1:1 to 15:1, more preferably 1:1 to 10:1.

The organic support may be any suitable polymer and in particular one which is stable under the conditions of use of the catalyst composition. Suitable polymer supports comprise styrene polymers, methacryate polymers, glycidyl methacrylate polymers, benzimidazole polymers, polyimides, polybenzothiazoles, polybenzoxazoles and the like, optionally copolymers with suitable comonomers and optionally cross-linked. The support may comprise a functionalised inorganic support such as functionalised silica or alumina. Preferably the support comprises a polybenzimidazole.

The catalyst composition according to the present invention may be prepared by effecting a ligand exchange reaction between an organometallic complex of molybdenum, vanadium, tungsten or titanium having a suitable leaving group with a support having imidazole ligands.

Pendant imidazole ligands may be attached to a support by functionalisation of the support by methods known in the art. Thus for example, a styrene polymer with, for example, a reactive halide substituent may be reacted with a suitable nucleophile such as an amine-substituted imidazole to attach the imidazole to the styrene polymer support. Similarly, a lithiated polystyrene may be reacted with an electrophilic imidazole to attach the imidazole ligand to the polystyrene support. A polymer support comprising glycidyl methacrylate polymer may be reacted with either an electrophilic or nucleophilic imidazole to attach the imidazole ligand thereto. Where the support is inorganic such as silica that may be functionalised with chloromethyl pyridine by methods known in the art and thereafter reacted with an electrophilic imidazole. Suitable preparation procedures are described for example by Sherrington, D. C. and Hodge, P. in "Polymer Supported Reactions in Organic Synthesis", Chichester J. Wiley (1980).

When the support comprises a polymer having an imidazole as part of its repeating unit, the support may be prepared by polymerisation of suitable monomers. For example polybenzimidazoles may be prepared by condensation of tetraamino compounds with diacids. See for example "Thermally Stable Polymers" by P. E. Cassidy and Marcel Dekker, New York (1980).

In the process of the present invention the catalyst may be activated before use by oxidising it with a suitable peroxide. The catalyst may also be activated 'in situ' by reaction with peroxide reactant.

The olefinic compound for use in the process of the present invention may be any organic olefinic compound having at least one olefinic double bond. The olefinic compound may be straight-chain, branched-chain or cyclic. The olefinic compound may be acyclic, monocyclic, bicyclic or polycyclic. The olefinic compound may be mono-olefinic, di-olefinic or polyolefinic. If more than one olefinic bond is present, the olefinic compound may be conjugated or non-conjugated. The olefinic compound may be substituted by an allylic hydroxyl, chloride, ether and/or ester group. The olefinic compound may be a vinyl ester, phenyl or nitrile compound. If substituted by electron-withdrawing groups for example nitrile, such groups should not be substituted directly on the olefinic double bond but should be remote therefrom. Preferably, any substituents are electron-donating. Preferably, the olefinic compound has the general formula (II):

where R and R' are the same or different and are independently hydrogen; hydrocarbyl groups, for example alkyl, aryl, alkylaryl, cycloalkyl or alkylcycloalkyl groups; substituted hydrocarbyl groups or together from a cyclic hydrocarbyl or substituted hydrocarbyl group. Suitably R and R' each have less than 30 carbon atoms. R and R' may together form a cycloalkyl or alkylcycloalkyl group suitably having less than 10 carbon atoms. One or both of the R and R' may independently have allylic hydroxyl, chloride, ether and/or ester substituent groups. One or both of R and R' may independently have vinyl ester, nitrile and/or phenyl substituent groups, but having regard to the above comments on electron withdrawing substituents.

Suitable olefinic compounds for use in the present invention may comprise one or more of ethylene, propylene, butenes, for example butene-1, cis or trans butene-2, pentenes, hexenes, octenes, decenes, cyclohexene, 4-vinylcyclohexene, unsaturated glycerin esters, allyl choride, styrenes methylene cyclohexane, cyclopentadiene and butadiene. A mixture of olefins may be used. The olefin may be used with minor amounts of impurities such as are known in the art, for example alkanes, aromatics, alcohols, ethers and acids but preferably, such impurities are inert to the reaction.

In the process of the present invention the peroxide may be any suitable source of peroxide, for example hydrogen peroxide, an organic hydroperoxide for example an alkyl hydroperoxide, a peroxide ether or a peracid. Preferably the peroxide is tert-butyl hydroperoxide, cumene hydroperoxide, ethylbenzene hydroperoxide or hydrogen peroxide.

The process of the present invention is particularly applicable to the epoxidation of propylene by tert-butyl hydroperoxide (TBHP) in the presence of low concentrations of tert-butyl alcohol (TBA); the TBHP and TBA being the product of isobutane oxidation and the TBA then being convertible to methyl tert-butyl ether (MTBE).

The process of the present invention may be performed in neat liquid reagents or a solvent may be used such as an aromatic, aliphatic, alcohol, alkane, ester, ketone or halogenated solvent with solvents such as 1,2 dichloromethane and toluene being preferred over t-butanol and methanol. Water can only be tolerated in small quantities and is preferably absent.

The process of the present invention may be performed at atmospheric or elevated pressure. Preferably, the process is performed at elevated pressure to maintain a suitable concentration of the olefinic compound in the liquid reaction medium if the olefinic compound is a gas at atmospheric pressure. A gas which is inert to the process such as nitrogen, helium, air or alkane may be used to maintain the elevated pressure. Suitably the operating pressure for the epoxidation of propylene is in the range atmospheric to 100 bar.

The process of the present invention may be performed at any suitable temperature depending upon the reagents used. Preferably, the process of the present invention is performed at a temperature in the range 20° to 500° C. Catalysts according to the present invention comprising molybdenum complexed to polybenzimidazole have shown high temperature stability up to 400° C. The process of the present invention may be performed as a batch or as a continuous process, preferably as a continuous process.

The molar ratio of peroxide to olefin may suitably be in the range 1:0.5 to 1:100 typically about 1:1 to 1:50. The molar ratio of catalyst to peroxide may be in the range 0.00001:1 to 1:1 typically about 0.002:1 to 0.03:1.

The invention will now be illustrated with reference to the following examples.

PREPARATION OF CATALYST COMPOSITION (PBI. Mo CATALYST)

Example 1

A catalyst composition according to the present invention comprising molybdenum complexed to a polybenzimidole microporous resin (PBI. Mo) was prepared in the following procedure.

10 g of wet polybenzimidizole microporous resin beads, AUROREZ (trade mark, Hoechst-Celanese) was stirred with 1N sodium hydroxide solution overnight, washed with deionised water until pH=7, washed with acetone and then dried in vacuo at 40°. The nitrogen content of the resin was then determined by microanalysis to be 15.15%, which, given that there are four nitrogen atoms in each polymer repeating unit, gives a repeating unit concentration of 2.71 mmolg$^{-1}$.

The resin was then refluxed in toluene for 72 hours with molybdenum acetyl acetonate $MoO_2(acac)_2$ at a molar ratio of organometallic complex:functional ligand of the resin of 2:1. Since for PBI there are two ligands per repeating unit, the ratio of organometallic complex:repeating unit of PBI was 4:1. The mother liquor turned blue. The resulting catalyst composition was then washed, with acetone using a Soxhlet extraction apparatus for approximately 48 hours. The resulting catalyst composition was dark blue with a few yellow beads dispersed throughout the resin.

The molybdenum content of the catalyst composition was determined by grinding the material, treating with aqua regia and making up the resultant solution with water before analysis using atomic absorption spectroscopy. The catalyst composition was found to have a metal loading of 1.88 mmol g-1. (In another preparation the metal loading was 3.24 mmolg$^{-1}$). In use, the amount of catalyst used was adjusted to give a constant metal concentration in the reaction mixture. The ligand loading for the PBI.Mo catalyst was calculated to be (1-weight molybdenum per gram)× ligand loading of the PBI resin=2.22 molg$^{-1}$ that is a ligand:metal ratio of 1.18:1.

The catalyst composition was activated prior to use in some experiments by refluxing a weighed amount of catalyst (containing 0.06 mmol molybdenum) with 5 mmol tetrabutyl hydroperoxide (1.3–1.4 ml solution prepared as hereinafter described) in 25 ml 1,2 chloroethane for a predetermined period. During activation the catalyst composition turned a yellow colour. When not in use, the activated catalyst compositions were stored in 5 mmol tert-butyl hydroperoxide (1.3–1.4 ml solution) and 10 ml dichloroethane.

Epoxidation of Cyclohexene

Epoxidation reactions were performed at 80° C. using the molybenum-loaded polybenzimidazole catalyst composition (PBI.Mo) previously prepared.

The peroxide used in the Experiments was an anhydrous solution of tert-butyl hydroperoxide in toluene which was prepared by swirling (to avoid formation of an emulsion) together 65 ml tert-butyl hydroperoxide-70 and 80 ml toluene in a 200 ml separating funnel. The aqueous layer (15 ml), was discarded and the organic layer (130 ml) was refluxed in a 250 ml flask fitted with a Dean-Stark trap for approximately 1 hour, during which 4 ml water was collected and discarded. Then a drying tube was fitted and a further 4 ml of distillate removed through a side arm. The remaining anhydrous solution (122 ml) was cooled and stored for use over 4 A molecular sieve. The molarity of the tert-butyl hydroperoxide solution was determined by iodiometry.

A 25 ml round-bottomed flask was used for the epoxidation reaction experiments, fitted with a reflux condenser and a water jacket connected to a temperature-controlled water recirculation bath to enable efficient and accurate temperature control.

In a typical epoxidation reaction approximately 0.2 g (0.06 mmmol molybdenum) of the catalyst composition (PBI.Mo), 8.4 ml of the olefin (0.083 mol cyclohexene). 0.2–0.3 ml 1,2 dichloroethane and 0.5 ml bromobenzene (internal standard for the gas chromatographic analysis of the reaction product) were all placed in the reaction vessel and allowed to equilibrate thermally (80° C.) for about 20 minutes. 5 mmol tert-butyl hydroperoxide (1.3–1.4 ml solution) was then added and the reaction was monitored by periodically withdrawing 1 microliter of the reaction mixture and injecting it onto a gas chromatograph to analyse the cyclohexene oxide concentration. A J&W Scientific DB-5 capillary column (30 m, internal diameter 0.32 mm, 1.0 micrometer thickness) was used with hydrogen carrier gas at 38 ml/min (40 kPa) and an oven temperature program of 100° C. (1 minute) then increasing to 120° C. at 40° C./minute. Each epoxidation was performed for a period of 4 hours. The yields of cyclohexene oxide were calculated as amount of cyclohexene oxide produced divided by the amount of tert-butyl hydroperoxide charged, expressed as a percentage.

To determine the amount of metal leached from the resin during the course of the reaction, at the end of the reaction the catalyst composition was filtered off and washed thoroughly, together with the reaction vessel, with 1,2 dichloroethane, the reaction composition and combined washings being placed in a rotary evaporator to remove the solvent and leave a yellow residue. This residue was treated with aqua regia (15 ml) for 48 hours before being diluted with water and analysed by atomic absorption spectroscopy.

Example 2

The yields of cyclohexene oxide for reactions at 80° C. using a catalyst composition which had not been activated and one which had been activated for 4 hours are given in Table 1.

TABLE 1

| | Example 2 | |
|---|---|---|
| Reaction Time | Yield of cyclohexene oxide (%) | |
| (Minutes) | Unactivated | 4 hour Activated |
| 20 | 60.6 | 79.6 |
| 40 | 92.3 | 92.2 |
| 60 | 97.1 | 96.0 |
| 80 | 98.8 | 97.0 |
| 100 | 100 | 98.0 |
| 120 | 99.9 | 97.8 |
| 180 | 98.7 | 99.5 |
| 240 | 98.3 | 99.2 |

Examples 3 to 6

A series of experiments was performed under the same conditions as Experiment 2 in which a PBI.Mo catalyst composition was re-used for up to ten reaction runs with the yields of cyclohexene oxide being monitored for alternate runs and metal leaching being monitored for each run. The catalyst was stored between runs in 5 mmol tert-butyl hydroperoxide/1,2 dichloroethane solution. The series was repeated for a catalyst composition which had not been activated (Example 3) and for catalyst compositions which had been activated for 4, 24 and 48 hours (Examples 4 to 6 respectively). The results are shown in Tables 2 to 6. These results show that increasing activation time for the catalyst results in an improvement in the re-usability of the catalyst such that with 48 hours activation, the catalyst shows an approximately constant final product yield over the last five reaction runs.

Whilst the 24 and 48 activated catalyst compositions show a high initial leaching of molybdenum, the leaching falls to zero after the third reaction run.

TABLE 2

Epoxidation using unactivated PBI.Mo catalyst
Example 3

| Reaction Time | Yield of cyclohexene oxide | | | | |
|---|---|---|---|---|---|
| (Minutes) | Run 1 | Run 3 | Run 5 | Run 7 | Run 9 |
| 20 | 15.7 | 2.4 | 0 | 0 | 0 |
| 40 | 56.2 | 6.6 | 0 | 0 | 0 |
| 60 | 77.4 | 18.6 | 0 | 1.4 | 0 |
| 80 | 90.2 | 35.4 | 1.9 | 4.3 | 0 |
| 100 | 95.9 | 50.3 | 9.8 | 9.7 | 0 |
| 120 | 96.8 | 64.7 | 20.2 | 10.8 | 0 |
| 180 | 100 | 92.9 | 40.5 | 49.8 | 1.0 |
| 240 | 99.3 | 100 | 72.6 | 82.7 | 1.9 |

TABLE 3

Epoxidation using 4 hour activated PBI.Mo catalyst
Example 4

| Reaction Time | Yield of cyclohexene oxide | | | | |
|---|---|---|---|---|---|
| (Minutes) | Run 1 | Run 3 | Run 5 | Run 7 | Run 9 |
| 20 | 79.6 | 48.5 | 0 | 0 | 0 |
| 40 | 92.2 | 63.0 | 2.2 | 2.4 | 2.1 |
| 60 | 96.0 | 79.1 | 3.5 | 3.7 | 2.2 |
| 80 | 97.1 | 83.9 | 4.6 | 4.5 | 2.7 |
| 100 | 98.0 | 91.2 | 8.6 | 6.9 | 4.4 |
| 120 | 97.8 | 97.9 | 24.6 | 15.7 | 5.3 |
| 180 | 99.5 | 99.9 | 78.0 | 68.1 | 10.4 |
| 240 | 99.2 | 99.1 | 96.1 | 92.8 | 44.4 |

TABLE 4

Epoxidation using 24 hour activated PBI.Mo catalyst
Example 5

| Reaction Time | Yield of cyclohexene oxide | | | | |
|---|---|---|---|---|---|
| (Minutes) | Run 1 | Run 3 | Run 5 | Run 7 | Run 9 |
| 20 | 33.6 | 44.7 | 8.8 | 6.8 | 19.4 |
| 40 | 30.8 | 52.4 | 10.6 | 7.0 | 19.2 |
| 60 | 55.4 | 65.5 | 18.6 | 8.7 | 19.8 |
| 80 | 72.8 | 74.0 | 34.1 | 8.8 | 19.2 |
| 100 | 79.1 | 86.7 | 52.8 | 11.2 | 23.5 |
| 120 | 86.1 | 87.1 | 69.6 | 14.9 | 23 |
| 180 | 96.8 | 100 | 87.5 | 27.5 | 34 |
| 240 | 100 | 95.3 | 84.8 | 53.2 | 46 |

TABLE 5

Epoxidation using 48 hour activated PBI.Mo catalyst
Example 6

| Reaction Time | Yield of cyclohexene oxide | | | | |
|---|---|---|---|---|---|
| (Minutes) | Run 1 | Run 3 | Run 5 | Run 7 | Run 9 |
| 20 | 65.0 | 38.3 | 7.1 | 10.9 | 23.6 |
| 40 | 82.8 | 52.6 | 8.0 | 8.7 | 23.4 |
| 60 | 94.5 | 62.7 | 10.4 | 13.7 | 30.0 |
| 80 | 96.5 | 73.2 | 16.1 | 13.7 | 42.4 |
| 100 | 100 | 76.0 | 29.1 | 20.9 | 51.6 |
| 120 | 99.3 | 79.9 | 46.3 | 30.2 | 58.6 |
| 180 | 98.2 | 100 | 76.7 | 61.3 | 81.5 |
| 240 | 93.9 | 85.7 | 100 | 94.5 | 94.0 |

TABLE 6

Metal Leaching data for epoxidations using PBI.Mo catalysts
Examples 3 to 6

| | Unactivated Catalyst | | 4 hour Activated Catalyst | | 24 hour Activated Catalyst | | 48 hour Activated Catalyst | |
|---|---|---|---|---|---|---|---|---|
| Run | Mo Leached ($\times 10^{-3}$ mmol) | % Mo Leached | Mo Leached ($\times 10^{-3}$ mmol) | % Mo Leached | Mo Leached ($\times 10^{-3}$ mmol) | % Mo Leached | Mo Leached ($\times 10^{-3}$ mmol) | % Mo Leached |
| 1 | — | 0 | 1.563 | 2.6 | 3.127 | 5.2 | 2.606 | 4.3 |
| 2 | — | 0 | 1.563 | 2.6 | 1.042 | 1.7 | 0.521 | 0.9 |
| 3 | — | 0 | 1.563 | 2.6 | — | 0 | — | 0 |
| 4 | — | 0 | 0.782 | 1.3 | — | 0 | — | 0 |
| 5 | — | 0 | — | 0 | — | 0 | — | 0 |
| 6 | — | 0 | — | 0 | — | 0 | — | 0 |
| 7 | — | 0 | — | 0 | — | 0 | — | 0 |
| 8 | — | 0 | — | 0 | — | 0 | — | 0 |
| 9 | — | 0 | — | 0 | — | 0 | — | 0 |
| 10 | — | 0 | — | 0 | — | 0 | — | 0 |

Example 7 and 8

A series of reaction runs was performed at different reaction temperatures for a PBI.Mo catalyst composition which had not been activated and for a PBI.Mo catalyst which had been activated for 4 hours. The results are shown in Tables 7 and 8.

TABLE 7

Temperature dependence of epoxidation
using unactivated PBI.Mo catalyst
Example 7

| Reaction Time | Yield of cyclohexene oxide | | | | |
|---|---|---|---|---|---|
| (Minutes) | 50° C. | 60° C. | 70° C. | 80° C. | 90° C. |
| 20 | 23.4 | 44.9 | 71.2 | 60.6 | 99.7 |
| 40 | 43.6 | 61.2 | 88.4 | 92.3 | 100 |
| 60 | 47.3 | 72.9 | 95.6 | 97.1 | 99.2 |
| 80 | 58.4 | 79.9 | 97.5 | 98.8 | 99.2 |
| 100 | 64.1 | 87.9 | 98.8 | 100 | 97.3 |
| 120 | 68.3 | 91.7 | 100 | 99.9 | 99.1 |
| 180 | 77.0 | 98.6 | 100 | 98.7 | 97.0 |
| 240 | 83.0 | 100 | 99.8 | 98.3 | 95.8 |

TABLE 8

Temperature dependence of epoxidation
using 4 hour activated PBI.Mo catalyst
Example 8

| Reaction Time | Yield of cyclohexene oxide | | | | |
|---|---|---|---|---|---|
| (Minutes) | 50° C. | 60° C. | 70° C. | 80° C. | 90° C. |
| 20 | 2.1 | 8.3 | 38.1 | 79.6 | 89.9 |
| 40 | 3.4 | 7.3 | 77.2 | 92.2 | 99.4 |
| 60 | 2.9 | 26.6 | 89.0 | 96.0 | 100 |
| 80 | 7.9 | 46.9 | 95.6 | 97.0 | 99.1 |
| 100 | 22.9 | 59.2 | 96.8 | 98.0 | 99.2 |
| 120 | 38.5 | 68.7 | 97.9 | 97.8 | 99.1 |
| 180 | 57.3 | 81.7 | 98.3 | 99.5 | 98.0 |
| 240 | 70.9 | 89.9 | 99.9 | 99.2 | 98.5 |

Comparative Experiment A

A comparative series of experiments was performed using molybdenum actylacetonate $MoO_2(acac)_2$ equivalent to 0.06 mmol Mo in place of the catalyst composition prepared as hereinbefore described at different temperatures. The results are shown in Table 9.

TABLE 9

Temperature dependence of epoxidation
using homogeneous $MoO_2(acac)_2$ catalyst
Comparative Experiment A

| Reaction Time | Yield of cyclohexene oxide (%) | | | | |
|---|---|---|---|---|---|
| (Minutes) | 50° C. | 60° C. | 70° C. | 80° C. | 90° C. |
| 20 | 44.1 | 52.1 | 77.8 | 87.8 | 99.0 |
| 40 | 59.7 | 67.6 | 84.9 | 91.7 | 99.2 |
| 60 | 69.7 | 77.3 | 88.2 | 90.9 | 98.3 |
| 80 | 75.3 | 82.7 | 89.4 | 92.0 | 100 |
| 100 | 79.6 | 87.6 | 91.9 | 97.4 | 97.4 |
| 120 | 84.0 | 91.2 | 92.7 | 97.9 | 96.3 |
| 180 | 91.1 | 96.1 | 96.0 | 92.9 | 97.6 |
| 240 | 95.6 | 100 | 100 | 100 | 96.0 |

Epoxidation of Oct-1-ene

Oct-1-ene was epoxidised using the same apparatus and experimental procedures as were used for epoxidation of cyclohexene.

The experiments were performed with the following reaction composition:

53.5 mmol oct-1-ene 0.06 mmol molybdenum (weight equivalent of catalyst)

5 mmol tert-butyl hydroperoxide 0.5 ml bromobenzene 1,2 dichloroethane solvent to total value of 10.5 ml.

Reaction temperature was 80° C. except when the effect of temperature was studied.

Reaction time was 4 hours.

Products analysed by GLC as before.

Comparative Experiment B

Oct-1-ene was epoxidised using a homogeneous $MoO_2(acac)_2$ catalyst as described above. The yields of epoxyoctane are given in Table 10. This is not an example according to the present invention.

TABLE 10

Epoxidation of Oct-1-ene
using homogeneous MoO$_2$(acac)$_2$ catalyst at 80° C.
Comparative Experiment B

| Reaction Time (Minutes) | Yield of epoxyoctane (%) |
|---|---|
| 20 | 88.0 |
| 40 | 90.0 |
| 60 | 94.0 |
| 80 | 98.0 |
| 100 | 100.0 |
| 120 | 100.0 |
| 180 | 100.0 |
| 240 | 100.0 |

Example 9

Example 8 was repeated using oct-1-ene and a PBI.Mo catalyst which had been activated for 4 hour as previously described. The results are shown in Table 11 and show the heterogeneous catalyst to be nearly as effective as the homogeneous catalyst.

TABLE 11

Epoxidation of Oct-1-ene using
PBI.Mo Catalyst at various temperatures
Example 9

| Reaction Time (Minutes) | Yield of cyclohexene oxide | | | |
|---|---|---|---|---|
| | 60° C. | 70° C. | 80° C. | 90° C. |
| 20 | 22.0 | 11.8 | 65.0 | 67.8 |
| 40 | 34.0 | 31.2 | 77.4 | 84.0 |
| 60 | 39.6 | 41.8 | 81.2 | 84.0 |
| 80 | 45.2 | 47.4 | 88.0 | 98.0 |
| 100 | 53.0 | 57.0 | 81.2 | 100.0 |
| 120 | 56.0 | 64.8 | 85.6 | 100.0 |
| 180 | 60.0 | 74.4 | 88.0 | 100.0 |
| 240 | 67.6 | 78.4 | 99.6 | 100.0 |

Example 10

Example 9 was repeated at 80° C. and 90° C. using PBI.Mo catalysts which had been activated for 24 hours. The results are shown in Table 12, together with the corresponding results for 4 hour activated catalyst from Example 9.

TABLE 12

Epoxidation of Oct-1-ene using
PBI.Mo Catalyst with different activation conditons
Example 10

| | Yield of cyclohexene oxide (%) | | | |
|---|---|---|---|---|
| Reaction Time | 80° C. | | 90° C. | |
| (Minutes) | 4 hr Activ. | 24 hr Activ. | 4 hr Activ. | 24 hr Activ. |
| 20 | 65.0 | 30.6 | 67.8 | 61.0 |
| 40 | 77.4 | 39.0 | 84.0 | 84.0 |
| 60 | 81.2 | 56.0 | 84.0 | 79.0 |
| 80 | 88.0 | 68.4 | 98.0 | 88.0 |
| 100 | 81.2 | 74.0 | 100.0 | 100.0 |
| 120 | 85.6 | 77.0 | 100.0 | 100.0 |
| 180 | 88.0 | 92.4 | 100.0 | 100.0 |
| 240 | 99.6 | 100.0 | 100.0 | 100.0 |

Epoxidation of Propylene

Propylene was epoxidised in a 50 ml stainless steel Parr autoclave fitted with a mechanical stirrer and a temperature controller at 400 psig. The autoclave was charged with the following reagents:

catalyst (weight equivalent to 0.12 mmol Mo)

1.0 ml chlorobenzene (GLC internal standard)

10 mmol tert-butyl hydroperoxide (2.6–2.8 ml of solution)

1,2 dichloroethane (17.2–17.4 ml to total volume of 21.0 ml).

The autoclave was cooled with an acetone/cardice ice bath. Propylene was transferred into a cooled (cardice/acetone) Fischer-Porter tube where it liquified and was measured. The Fischer-Porter tube was then warmed to transfer the measured aliquot (238 mmol) of propylene to the cooled autoclave. When the transfer was complete the autoclave was warmed to room temperature and pressurised to 300 psi with helium. The autoclave was then heated to the required reaction temperature (typically 80° C. with a corresponding pressure of 400 psi) at which point reaction commenced. After the desired reaction time had elapsed, the autoclave was cooled to –5° C. with an ice/acetone bath and the autoclave gases slowly vented off. The autoclave was dismantled and its contents transferred to a flask in an ice bath to retain volatiles. The autoclave product was analysed for propylene oxide by gas chromatography. (J & W DB5 capillary column with gas rates as previously described; oven at 70° C. (1 min) then 45° C./min to 120° C.). The yield was based on conversion of tert butyl hydroperoxide i.e. 10 mmol tert-butyl hydroperoxide equivalent to 10 mmol propylene oxide=100% conversion.

Example 11

The yield of propylene oxide was determined at the end of each experiment of differing duration for unactivated PBI.Mo catalyst and for a corresponding amount of homogeneous MoO$_2$(acac)$_2$ catalyst. The results, in Table 13 show that the unactivated catalyst achieves a yield of propylene oxide comparable to that achieved with the homogeneous catalyst for reactions of 4 hours duration and that it appears to exhibit a slightly faster initial rate of reaction than the homogeneous catalyst.

TABLE 13

Experimental Data for Example 11

| Time | Propylene Oxide Yield (%) | |
|---|---|---|
| (hours) | MoO$_2$(acac)$_2$ | PBI.Mo |
| 1 | 47.6 | 89.4 |
| 2 | 77.1 | 90.6 |
| 3 | 91.7 | 83.4 |
| 4 | 100 | 92.6 |

Example 12

The yield of propylene oxide was measured for a series of 10 epoxidations as Example 11 but using a reaction time of 1 hour using the same catalyst for each reaction. The catalyst had not been activated and was separated from the reaction mixture after each reaction run by filtration and was stored in a solution of 10 mmol of tert-butyl hydroperoxide in 1,2 dichloroethane between runs. The results, shown in Table 14, show an increase in yield and activity as the catalyst was reused. The amount of molybdenum leached during these epoxidations was determined as previously described by placing the reaction mixture and combined washings in a rotary evaporator and removing all the solvents to leave a yellow residue which was treated with aqua regia, diluted with deionised water and analysed by atomic absorption spectroscopy.

The results, shown in Table 14 show that after 2 runs the leaching stops.

TABLE 14

Experimental Data for Example 12

| Run | Propylene Oxide Yield (%) | Mo Leached (%) |
|---|---|---|
| 1 | 59.0 | 2.9 |
| 2 | 68.4 | 0 |
| 3 | 74.8 | 0 |
| 4 | 74.1 | 0 |
| 5 | 80.4 | 0 |
| 6 | 84.6 | 0 |
| 7 | 87.4 | 0 |
| 8 | 89.7 | 0 |
| 9 | 94.8 | 0 |
| 10 | 99.8 | 0 |

Comparative Experiment C

Example 12 was repeated again using reaction times of 1 hour, using a catalyst comprising molybdenum supported on a functionalised polystyrene chelating resin which has a repeating unit represented by the general formula:

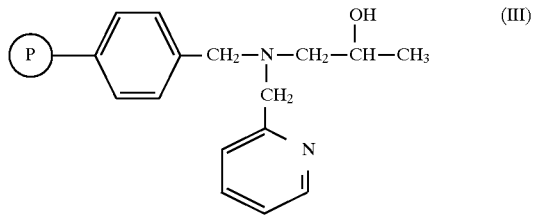

(III)

where Ⓟ represents the polymer backbone. This catalyst had been activated for 4 hours. The use of this catalyst for the epoxidation of cyclohexene is described by Sherrington and Simpson in Journal of Catalysis (131) 115 (1991). This is not a catalyst according to the present invention because the molybdenum is not complexed through the intermediacy of an imidazole ligand.

The results are shown in Table 15 and show catalyst activity progressively decreasing and constant, prolonged metal leaching with repeated use. This catalyst is therefore inferior to the catalyst according to the present invention described in Experiment 12.

TABLE 15

Experimental Data for Epoxidation of Propene using Ps.Mo Catalyst Comparative Experiment C

| Run | Propylene Oxide Yield (%) | Mo Leached (%) |
|---|---|---|
| 1 | 98.7 | 2.9 |
| 2 | 85.8 | 2.2 |
| 3 | 90.1 | 2.2 |
| 4 | 79.9 | 3.6 |
| 5 | 91.3 | 4.4 |
| 6 | 99.0 | 2.2 |

TABLE 15-continued

Experimental Data for Epoxidation of Propene using Ps.Mo Catalyst Comparative Experiment C

| Run | Propylene Oxide Yield (%) | Mo Leached (%) |
|---|---|---|
| 7 | 65.2 | 2.9 |
| 8 | 85.9 | 0.7 |
| 9 | 87.0 | 0.7 |
| 10 |  | 0.7 |

NB Blank space where no data is available.

Example 13

Preparation of Catalyst Compositions Having Molybdenum Supported by Pendant Imidazole Ligands on Organic Polymer Supports Catalyst compositions having molybdenum supported by pendant imidazole ligands on organic polymers, polystyrene (Ps) and polylglycidyl methacrylate) (PGMA) were prepared by the following procedures:

(a) Preparation of Macroreticular Chloromethylated Polystyrene

This functionalised resin was prepared by the suspension copolymerisation of vinylbenzene chloride and divinylbenzene as follows:

Synthesis of stabilising solution (or bulk phase): 9 g boric acid was dissolved in 378 ml deionised H$_2$O and aqueous cellosize solution (12 g, 0.17% w/v) added. The pH of the solution was adjusted to 10.3 using 50% aqueous NaOH solution. Xanthan gum solution (300 ml, 0.3% w/v) was added along with NaCl (120 g). The resulting solution was stirred in a 1 liter suspension polymerisation reactor at a temperature of 80° C. for a period of 1 hour prior to the addition of the monomer/diluent solution.

Monomer/diluent solution: 60 ml vinylbenzene chloride, 40 ml divinylbenzene and 50 ml 2-ethylhexanol stirred in flask. AIBN initiator added (1 g) and solution stirred until AIBN dissolved.

The solution was slowly added to the stirred bulk phase dropwise using an addition funnel. The resulting polymerisation mixture was left for a period of 5 hours at a temperature of 80° C. Upon completion, the resulting beads were filtered off using a 100 μm sieve, washed thoroughly with water and acetone, and extracted with acetone in a Soxhlet apparatus for a period of 24 hours before being dried in vacuo at 40° C.

The functionalised resin was used in the preparation of organic polymer supports having pendant imidazole ligands.

(b) Preparation of Poly(glycidyl methacrylate) PGMA

Macroreticular poly(glycidyl methacrylate) crosslinked with 40% ethylene glycol dimethylacrylate was synthesised by suspension polymerisation of a mixture of glycidyl methacrylate and ethylene glycol dimethacrylate (6/4 vol/vol) with a mixture of cyclohexanol and dodecanol (9/1 vol/vol) as the porogen (monomer-diluent, 1/1 vol/vol).

Biozan Gum R was used as stabiliser and a resin having a particle size of 300–800 μm was obtained. This procedure is described by D. Lindsay and D. C. Sherrington in Reactive Polymers 1985 3, 327–339.

This resin was used in the preparation of organic polymer supports having pendant imidazole ligands.

(c) Preparation of 2-pyridyl-2-imidazole ligand.

This ligand was synthesised according to the procedure in South Africa Patent 77/5398 as follows:

Ice-cold solutions of 2-pyridine carboxaldehyde (78 ml, 0.79 mol), glyoxal (120 ml) and ethanol (100 ml) were mixed in a 3-necked, 1 liter round-bottom flask under a nitrogen atmosphere. Concentrated ammonia solution (120 ml, 2.16 mol) was added, and the flask maintained at 0° C. for 30 minutes with continuous stirring, until the initial vigorous reaction died down. The flask was stoppered, retaining the nitrogen atmosphere, and stirred at room temperature for 3 hours.

Excess ethanol (appox. 100 ml) was removed and the remaining dark brown liquid extracted with 200 ml portions of ether 10 times. The ether extracts were dried with magnesium sulphate prior to the ether being removed by evaporation to yield a brown solid, which was recrystallised using ethyl acetate.

This imidazole ligand was used in the preparation of organic polymer supports having pendant imidazole ligands.

(d) Functionalisation of macroreticular chloromethylated polystyrene and poly(glycidyl methacrylate) resins with imidazole ligands.

The chloromethylated polystyrene (Ps) and poly(glycidyl methacrylate) (PGMA) resins were functionalised with the following imidazole ligands imidazole (Im), benzimidazole (BzIm), 2-pyridyl-2-imidazole (PyIm) and 5-benzimidazole carboxylic acid (5BzCOOH) as follows:

Chloromethylated Polystyrene (Ps)

Ps resin (5 g, 0.021 mol —$CH_2Cl$) was refluxed with the ligand (0.063 mol, 3:1 ligand:—$CH_2Cl$) in toluene (120 ml) for a period of 12 hours. The resultant support was extracted with acetone in a Soxhlet apparatus for 24 hours and dried in vacuo at 40° C.

Poly(Glycidyl Methacrylate)

PGMA resin (5 g, 0.020 mol epoxide group) was refluxed with the ligand (0.040 mol, 2:1 ligand:epoxide group) in toluene (120 ml) for a period of 12 hours. The resultant support was extracted with acetone in a Soxhlet apparatus for 24 hours and dried in vaccuo at 40° C.

(e) Attachment of 5-benzimidazole carboxylic acid (5BzCOOH) to chloromethylated polystyrene (Ps)

5-Benzimidazole carboxylic acid (6.804 g, 0.042 mol) and NaOH (1.68 g, 0.042 mol) (1:1 molar ratio employed in order to ensure deprotonation of carboxylic acid group only) were stirred in 150 ml ethanol for 4 hours in a flask fitted with a drying tube. Ps resin (5 g, 0.021 mol —$CH_2Cl$) was added and mixture refluxed for 24 hours. The resultant support was extracted with acetone in Soxhlet apparatus for 48 hours and dried in vacuo at 40° C.

(f) Polymer Supports.

Microanalytical, ligand loading and IR data for the functionalised polymer supports are given in Table 16.

TABLE 16

Elemental microanalysis, ligand loading and IR data for functionalised polymer support resins.

| Resin | % C | % H | % N | Ligand Loading (mmol g$^{-1}$) | IR |
|---|---|---|---|---|---|
| Ps.Im | 74.8 | 6.8 | 3.6 | 1.30 | 1260 cm$^{-1}$ loss of —$CH_2Cl$ wag<br>1550 cm$^{-1}$ C=N str. |

TABLE 16-continued

Elemental microanalysis, ligand loading and IR data for functionalised polymer support resins.

| Resin | % C | % H | % N | Ligand Loading (mmol g$^{-1}$) | IR |
|---|---|---|---|---|---|
| Ps.BzIm | 72.8 | 6.9 | 3.8 | 1.34 | 750 cm$^{-1}$ arom. ring str. |
| Ps.PyIm | 71.2 | 5.9 | 9.2 | 2.19 | 1450 cm$^{-1}$ C=N str. |
| Ps.5BzCOOH | 74.8 | 6.3 | 1.8 | 0.42 | 3440 cm$^{-1}$ N—H str.<br>1590 cm$^{-1}$ C=O str. |
| PGMA.Im | 54.0 | 6.8 | 5.7 | 2.04 | 3400 cm$^{-1}$ OH str.<br>1550 cm'-1 C=N str. |
| PGMA.BzIm | 57.0 | 6.3 | 4.7 | 1.67 | 750 cm$^{-1}$ arom. ring str. |
| PGMA.PyIm | 56.0 | 6.3 | 4.5 | 1.06 | 1450 cm$^{-1}$ C=N str. |

(g) Preparation of Catalyst Compositions

Catalyst compositions were prepared by refluxing the organic polymer support with a 2:1 molar excess of metal acetylacetonate before being washed with acetone in a Soxhlet apparatus.

During the preparation of all the supported Mo catalyst compositions it was noted that the colour of the reaction solution turned dark blue in all cases. This colour was also detected in the initial extraction solvent in the Soxhlet apparatus but disappeared after the introduction of fresh solvent.

IR spectra of all the supported complexes were recorded, and salient data from these, along with the colours of the complexes, are listed in Table 17. Metal and ligand loadings are given in Table 18.

TABLE 17

IR Data for Molybdenum supported on organic polymer supports.

| Complex | Colour | Mo=O str. (cm$^{-1}$) | Mo—O—Mo str. (cm$^{-1}$) |
|---|---|---|---|
| Ps.Im.Mo | Brown | 960 910 | — |
| Ps.BzIm.Mo | Green | 956 910 | — |
| Ps.PyIm.Mo | Brown | 960 915 | — |
| Ps.5BzCOO.Mo | Green | 960 904 | — |
| PGMA.Im.Mo | Green | 957 906 | — |
| PGMA.BzIm.Mo | Green | 953 916 | — |
| PGMA.PyIm.Mo | Green | 946 910 | — |
| PBI.Mo | Dark Blue[1] | 950 979 | — |

[1]There were also some yellow beads dispersed throughout the resin.

TABLE 18

Metal Loading Data for molybdenum supported on organic polymer supports

| Complex | Metal Loading (mmol g$^{-1}$) | Metal Loading (g g$^{-1}$) | Ligand Loading[a] (mmol g$^{-1}$) | Ligand:Metal Ion Ratio |
|---|---|---|---|---|
| Ps.Im.Mo | 0.77 | 0.074 | 1.20 | 1.56:1 |
| Ps.BzIm.Mo | 0.93 | 0.089 | 1.22 | 1.31:1 |
| Ps.PyIm.Mo | 0.47 | 0.045 | 2.09 | 4.45:1 |
| Ps.5BzCOO.Mo | 0.19 | 0.019 | 0.41 | 2.16:1 |
| PGMA.Im.Mo | 0.46 | 0.094 | 1.95 | 4.26:1 |

TABLE 18-continued

Metal Loading Data for molybdenum supported on organic polymer supports

| Complex | Metal Loading (mmol g$^{-1}$) | Metal Loading (g g$^{-1}$) | Ligand Loading[a] (mmol g$^{-1}$) | Ligand:Metal Ion Ratio |
|---|---|---|---|---|
| PGMA.BzIm.Mo | 0.20 | 0.019 | 1.64 | 8.27:1 |
| PGMA.PyIm.Mo | 0.66 | 0.063 | 0.99 | 1.49:1 |

[a](1-weight Mo per gram supported complex) × (original ligand loading)

When required, the polymer-supported molybdenum was subjected to an activation procedure prior to use in an epoxidation. An exact weight (containing 0.06 mmol Mo) of each complex was refluxed for a known period with TBHP (5 mmol, 1.3–1.4 ml) in 1,2dichloroethane (25 ml). When not in use in an epoxidation, the activated catalyst was stored in TBHP (5 mmol, 1.3–1.4 ml) and 1,2 dichloroethane (10 ml). During the activation process the colour of all the complexes changed to yellow without exception.

A catalyst according to the present invention having pendant 2-pyridyl imidazole ligands was prepared as above described and had a repeating unit represented by the general formula (IV):

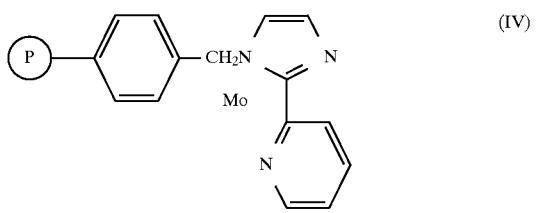

wherein Ⓟ represents a macroreticular polystyrene backbone.

The catalyst thus prepared having repeating units represented by general formula (IV) was designated PsPyImMo and had 2.09 mmol ligand g$^{-1}$ and 0.47 mmol Mo g$^{-1}$.

A catalyst according to the present invention having pendant benzimidazole ligands prepared was prepared as described above and had repeating unit represented by the general formula (V):

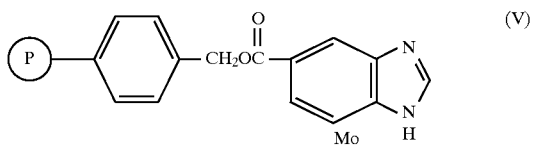

wherein Ⓟ represents a macroreticular polystyrene backbone. The catalyst having repeating units represented by general formula (V) was designated Ps5BzCOOMo and had 0.41 mmol ligand g$^{-1}$ and 0.19 mmole Mo g$^{-1}$.

Example 14

Epoxidation of Cyclohexene

Experiment 2 was repeated using the catalyst compositions prepared in Example 13. The results are given in Table 19, together with the results from Example 2. Yields were based on tertbutyl hydroperoxide conversion. Reaction conditions were 0.5 mmol of tertbutyl hydroperoxide, 83 mmol of cyclohexene, 0.06 mmol of catalyst and 80° C. temperature.

TABLE 19

Epoxidations of Cyclohexene

| Catalyst | Activation Conditions | Cyclohexene Oxide Yield (%) 20 min | 60 min | 240 min |
|---|---|---|---|---|
| PBI.Mo | Unact. | 60.6 | 97.1 | 98.3 |
| | 4 hr act. | 79.6 | 96.0 | 99.2 |
| Ps.Im.Mo | Unact. | 1.9 | 3.1 | 24.0 |
| | 4 hr act. | 14.9 | 20.0 | 95.7 |
| Ps.BzIm.Mo | Unact. | 1.9 | 3.1 | 24.0 |
| | 4 hr act. | 14.5 | 20.7 | 87.8 |
| Ps.PyIm.Mo | Unact. | 19.6 | 26.4 | 87.8 |
| | 4 hr act. | 6.7 | 9.3 | 74.1 |
| Ps.5BzCOO.Mo | Unact. | 3.4 | 23.8 | 100.0 |
| | 4 hr act. | 11.6 | 41.5 | 100.0 |
| PGMA.Im.Mo | Unact. | 4.5 | 22.8 | 83.6 |
| | 4 hr act. | 10.0 | 29.0 | 92.0 |
| PGMA.BzIm.Mo | Unact. | 17.2 | 37.4 | 60.7 |
| | 4 hr act. | 21.4 | 52.9 | 89.5 |
| PGMA.PyIm.Mo | Unact. | 53.9 | 84.9 | 100.0 |
| | 4 hr act. | 42.3 | 87.6 | 100.0 |

Example 15

Epoxidation of Propene Using PsPyImMo Catalyst

PsPyIm Mo catalyst prepared in Example 13 was used as catalyst for the epoxidation of propene using t-butylhydroperoxide.

The reaction conditions were 10 mmol t-butylhydroperoxide, 0.12 mmol molybdenum in the catalyst, 238 mmol propene; temperature 80° C. and pressure 400 psi using helium).

The catalyst was used and reused in a series of epoxidation runs each of 1 hour. The catalyst was activated for 4 hours as previously described prior to the initial epoxidation run. The results, shown in Table 20 show the catalyst to have high activity and selectivity for propene epoxidation. There was no molybdenum leaching.

Turnover frequency (TOF) is the moles of product produced per unit time divided by moles of active catalyst, which as metal leaching is negligible is approximately moles of product produced per unit time divided by moles of metal originally present. 50% TOF was calculated as 50% of material converted/time taken, per mol. Mo used in catalyst.

TABLE 20

Catalyst recycling experiments-epoxidation of propene using Ps.PyIm.Mo catalyst Example 15

| Run | Propylene Oxide Yield (%) | Mo Leached (%) | Turnover Frequency (mol epoxide min$^{-1}$ mol Mo$^{-1}$) |
|---|---|---|---|
| 1 | 98.9 | 0 | 1.37 |
| 2 | 95.3 | 0 | 1.32 |
| 3 | 97.7 | 0 | 1.36 |
| 4 | — | 0 | — |
| 5 | 95.0 | 0 | 1.32 |
| 6 | — | 0 | — |
| 7 | 93.4 | 0 | 1.30 |
| 8 | 92.8 | 0 | 1.29 |
| 9 | 92.8 | 0 | 1.29 |
| 10 | — | 0 | — |

— = data were not obtained.

Example 16

Epoxidation of Propene Using Ps5BzCOOMo Catalyst

Example 15 was repeated using Ps5BzCOOMo catalyst prepared in Example 13. The catalyst was not activated prior to the initial epoxidation run. The results shown in Table 21 show the catalyst to have high activity and selectivity for propene epoxidation. The molybdenum leaching was negligible.

TABLE 21

Catalyst recycling experiments-epoxidation of propene using Ps5BzCOOMo catalyst Example 16

| Run | Propylene Oxide Yield (%) | Mo Leached (%) | Turnover Frequency (mol epoxide min$^{-1}$ mol Mo$^{-1}$) |
|---|---|---|---|
| 1 | 100.0 | 1.1 | 1.39 |
| 2 | 88.0 | 1.1 | 1.22 |
| 3 | 87.4 | 1.1 | 1.21 |
| 4 | — | 0 | — |
| 5 | 86.5 | 0 | 1.20 |
| 6 | 84.9 | 0 | 1.18 |
| 7 | 85.5 | 0 | 1.19 |
| 8 | 86.5 | 0 | 1.20 |
| 9 | 86.2 | 0 | 1.20 |
| 10 | 88.2 | 0 | 1.20 |

— = data were not obtained.

Example 17

Epoxidation of Propene Using PGMA PyIm.Mo Catalyst

Example 15 was repeated using PGMA.PyIm.Mo prepared in Example 13 which was not activated prior to the initial epoxidation. The results are shown in Table 22.

TABLE 22

Catalyst recycling experiments-Epoxidation of propene using PGMA.PyIm.Mo catalyst.

| Run | Propylene Oxide Yield (%) | Mo Leached (%) | Turnover Frequency (mol epoxide min$^{-1}$ mol Mo$^{-1}$) |
|---|---|---|---|
| 1 | 90.1 | 1.1 | 1.25 |
| 2 | 89.3 | 1.1 | 1.24 |
| 3 | 74.1 | 0 | 1.03 |
| 4 | —(a) | 0 | —(a) |
| 5 | 43.4 | 0 | 0.60 |
| 6 | 53.6 | 0 | 0.74 |
| 7 | —(a) | 0 | —(a) |
| 8 | 55.4 | 0 | 0.77 |
| 9 | 53.8 | 0 | 0.75 |
| 10 | 53.9 | 0 | 0.75 |

(a)— = data were not obtained.

Comparative Example D

Epoxidation of Propene Using PGMA.AMP.Mo Catalyst

Example 15 was repeated using a catalyst comprising molybdenum supported on polyglycidyl methacrate functionalised with 2-aminomethyl pyridine. PGMA.AMP.Mo which had been activated for 4 hours before use. This is not an example according to the present invention. The results for 1 hour reaction twice are shown in Table 23.

TABLE 23

Catalyst recycling experiments-Epoxidation of propene using PGMA.AMP.Mo catalyst

| Run | Propylene Oxide Yield (%) | Mo Leached (%) | Turnover Frequency (mol epoxide min$^{-1}$ mol Mo$^{-1}$) |
|---|---|---|---|
| 1 | 84.5 | 0.7 | 1.17 |
| 2 | 82.8 | 0.7 | 1.15 |
| 3 | 94.8 | 0.7 | 1.32 |
| 4 | 88.6 | 0.7 | 1.23 |
| 5 | 96.6 | 0.7 | 1.34 |
| 6 | 93.6 | 0.7 | 1.30 |
| 7 | 99.0 | 2.1 | 1.38 |
| 8 | 83.9 | 0.7 | 1.17 |
| 9 | 82.0 | 0 | 1.14 |
| 10 | 81.7 | 0 | 1.13 |

Further Epoxidations

In these epoxidations, a double-necked, round-bottom flask, which was surrounded with an adiabatic jacket, was used. This flask was connected to an external heating bath's pump by rubber tubes. In all the epoxidations temperature was kept constant at 60.0°±0.1° C. except in the case of allyl chloride, which has a boiling point of 45° C. To make the flask accessible for sample collecting, a stopper with a septum was placed at the second neck. A reflux condenser was fitted to the flask and stirring was by an overhead stirrer. The use of a stirrer caused the polymer beads to break up during the experiments.

No attempt was made to protect the reaction mixtures against atmospheric oxygen.

(a) 4-vinyl-cyclohexene 0.0803 g of PBI.Mo catalyst prepared as previously described; 7.5 ml of 4-vinyl-cyclohexene; 0.5 ml of bromobenzene and 0.55 ml of toluene was placed in the flask. The solution was allowed to reach thermal equilibrium for 30 minutes, then 1.42 ml of tert-butyl hydroperoxide/toluene solution (3.52M) was added. Samples were analysed at intervals by gc. It was estimated that the 50% turnover frequency was between 0.14 and 0.59 moles 4-vinyl cyclohexene per mol Mo per minute. At least 7 small impurities were detected in the 4-vinyl-cyclohexene. No measurable amount of 4-vinyl-cyclohexene dioxide was observed (i.e. conversion to this product less than 0.2%). After 57 hours the major product was 4-vinylcyclohexene monoxide together with four other unidentified compounds.

(b) Methylene-cyclohexane

The previous experiment was repeated using 0.0805 g PBIMo; 2 ml methylene-cyclohexane; 0.5 ml bromobenzene; 5.58 ml toluene and 1.42 ml of tert-butyl hydroperoxide/toluene solution (3.52M). Samples withdrawn from the reaction flask were collected in vials immersed in dry ice/acetone to stop reaction. The epoxidation proceeded with almost no side reactions and the 50% turnover frequency was 0.127 moles cyclohexene/mole Mo/minute. In this epoxidation, the concentration of olefin is less than in other epoxidations. The experiment was repeated using 7.5 ml methylene cyclohexane;0.50 ml bromobenzene;0.67 ml toluene; 1.33 ml tert-butyl hydroperoxide/toluene solution (3.75M) and 0.040 g PBIMo=0.00440 mmole Mo. The main product was 1-oxo spiro [2,5] octane at a 50% turnover frequency of 0.60 mole epoxide/mole Mo/min.(c)

Allyl-Chloride

Since allyl-chloride boils at 45° C., it was boiled off during the epoxidation with the heating jacket at 60° C. Thus after 5 hours more than half of the allyl chloride had disappeared and after 20 hours the reaction mixture was almost down to dryness with significant loss of epichlorohydrin.

Otherwise the previous procedure was used with 0.080 g of PBIMo; 7.5 ml of allyl-chloride; 0.5 ml of bromobenzene; 0.60 ml of toluene and 1.40 ml of tertbutyl hydroperoxide solution (3.52M).

The epoxidation proceeded but due to the vaporisation of allyl chloride, it was only possible to estimate the 50% turnover frequency to be more than 0.21 moles clyclohexene per mole Mo per minute at 45° C.

(d) Styrene

The previous experiment was repeated using 7.50 ml styrene; 0.50 ml bromobenzene; 0.68 ml toluene; 1.32 ml tertbutyl hydroperoxide/toluene solution (3.79M) and 0.0406 g PBIMo=0.00447 mole Mo. A 50% turnover frequency of 0.33 mol. styrene/mol Mo/min as obtained.

We claim:

1. A catalyst for the epoxidation of olefinic compounds comprising a metal selected from the group consisting of molybdenum, vanadium, tungsten, titanium and mixtures thereof, complexed to an organic or inorganic support through the intermediacy of a pendant imidazole ligand, said catalyst having epoxidation activity.

2. A catalyst composition as claimed in claim 1 in which the imidazole ligand is selected from the group consisting of unsubstituted imidazole, 2-pyridyl imidazole, benzimidazole, hydroxy-substituted imidazole, hydroxy-substituted benzimidazole and 5-benzimidazole carboxylic acid.

3. A catalyst composition as claimed in claim 2 in which the support comprises an organic polymer.

4. A catalyst composition as claimed in claim 3 in which the polymer support is selected from the group consisting of styrene polymers and glycidyl methacrylate polymers.

5. A catalyst composition as claimed in claim 4 in which the imidazole ligand is selected from the group consisting of imidazole, 2-pyridyl imidazole, benzimidazole and 5-benzimidazole carboxylic acid.

* * * * *